(12) United States Patent
Wang (10) Patent No.: US 12,036,032 B2
(45) Date of Patent: Jul. 16, 2024

(54) DETECTION DEVICE AND DETECTION METHOD FOR FUSION OF TACTILE SENSING AND OPTICAL TOMOGRAPHY

(71) Applicant: NANJING STARTON TECHNOLOGY CO. LTD., Nanjing (CN)

(72) Inventor: Weiping Wang, Nanjing (CN)

(73) Assignee: NANJING STARTON TECHNOLOGY CO.LTD., Nanjing (CN)

( * ) Notice: Subject to any disclaimer, the term of this patent is extended or adjusted under 35 U.S.C. 154(b) by 1024 days.

(21) Appl. No.: 16/963,825

(22) PCT Filed: Aug. 28, 2019

(86) PCT No.: PCT/CN2019/102952
§ 371 (c)(1),
(2) Date: Jul. 21, 2020

(87) PCT Pub. No.: WO2020/043115
PCT Pub. Date: Mar. 5, 2020

(65) Prior Publication Data
US 2021/0052210 A1    Feb. 25, 2021

(30) Foreign Application Priority Data

Aug. 28, 2018  (CN) .......................... 201810987944.0

(51) Int. Cl.
*A61B 5/00* (2006.01)
(52) U.S. Cl.
CPC .......... *A61B 5/4312* (2013.01); *A61B 5/0033* (2013.01); *A61B 5/0053* (2013.01); *A61B 5/0073* (2013.01)

(58) Field of Classification Search
None
See application file for complete search history.

(56) References Cited

U.S. PATENT DOCUMENTS 6,595,933 B2    7/2003  Sarvazyan et al.
2001/0031934 A1*  10/2001  Sarvazyan ........... A61B 5/4312
600/587
(Continued)

FOREIGN PATENT DOCUMENTS

| CN | 101172047 A | 5/2008 |
| CN | 106214130 A | 12/2016 |

(Continued)

*Primary Examiner* — Devin B Henson
*Assistant Examiner* — Matthew Eric Ogles
(74) *Attorney, Agent, or Firm* — Bayramoglu Law Offices LLC (57) ABSTRACT

A detection device for fusion of tactile sensing and optical tomography includes a handheld probe, a controller for performing signal control and data acquisition on the handheld probe and communicating with a computer, and the computer for performing data analysis and image reconstruction and display on controller information. The handheld probe includes a probe front cover. A tactile sensor, a probe base, and a photoelectric sensor module disposed in sequence are sandwiched between a first probe side cover and a second probe side cover matching the probe front cover. An optical fiber connected to the photoelectric sensor module is interposed between the first probe side cover and the second probe side cover. A detection method based on the detection device comprises detecting tumors inside biological tissue, and detecting physical changes (i.e. local hardness) of the tissue and functional changes (i.e. blood supply distribution) of the tissue.

14 Claims, 5 Drawing Sheets

(56) References Cited

U.S. PATENT DOCUMENTS

| | | | | |
|---|---|---|---|---|
| 2008/0058638 A1* | 3/2008 | Zhu | ............... | G01N 21/6428 |
| | | | | 600/425 |
| 2016/0228008 A1* | 8/2016 | Lee | ............... | A61B 5/0053 |
| 2019/0125245 A1* | 5/2019 | Kim | ............... | A61B 5/0091 |
| 2019/0150749 A1* | 5/2019 | Harris | ............ | A61B 5/0095 |

FOREIGN PATENT DOCUMENTS

| CN | 106264436 A | 1/2017 |
|---|---|---|
| CN | 109044282 A | 12/2018 |
| CN | 209252833 U | 8/2019 |

\* cited by examiner

DETECTION DEVICE AND DETECTION METHOD FOR FUSION OF TACTILE SENSING AND OPTICAL TOMOGRAPHY

CROSS REFERENCE TO THE RELATED APPLICATIONS

This application is the national phase entry of International Application PCT/CN2019/102952, filed on Aug. 28, 2019, which is based upon and claims priority to Chinese Patent Application No. 201810987944.0, filed on Aug. 28, 2018, the entire contents of which are incorporated herein by reference.

TECHNICAL FIELD

The present invention belongs to the field of biomedical imaging, and in particular to a dual-mode imaging device that uses a tactile (pressure) array sensor and optical tomography imaging to display a biological tissue structure and absorption and scattering of different light, and a control and imaging method based on the device. A typical application of the invention is the detection of breast tumor diseases.

BACKGROUND

In imaging examinations of biological tissue such as mammary gland (breast) tissue, a commonly used detection apparatus includes mammary gland molybdenum target X-ray imaging, ultrasound imaging, optical imaging, and nuclear magnetic resonance (MRI). Among them, the mammary gland molybdenum target X-ray imaging has a wide range of detection levels, easy imaging, and repeatability, and is the new standard for breast cancer examinations. However, the molybdenum target X-ray imaging has X-ray radiation, which requires special protective use environment, and the examination effect on dense breasts is not good. Ultrasound and nuclear magnetic resonance (MRI) also play a complementary role in the diagnosis of breast cancers. Nuclear magnetic resonance has an obvious sensitivity advantage, but its use is time-consuming and expensive. Ultrasound is the most commonly used medical imaging apparatus, is suitable for use in different occasions, has cost and price advantages, and is often used for breast cancer examinations. However, the use of conventional ultrasound systems in mammary gland examinations has been limited in several aspects: on the one hand, it requires high image recognition skills of the doctors, and on the other hand, the imaging lacks reproducibility. The commonly used breast ultrasound in clinical practice is mainly two-dimensional B-mode ultrasound. This traditional ultrasound imaging mode can only provide an image of a certain section of the breast, and has certain limitations.

A common clinical method of breast tumor examinations is palpation by the doctors. A doctor can feel whether there is a lump or not inside the breast through the doctor's hand. This clinical palpation can find the lump, and the experienced doctor can judge the characteristics of the lump based on the palpation feeling of the lump. Based on this principle, the United States has produced two products, one being SureTouch and one being iBE. Based on a distributed pressure sensor technology, stress changes of the tissue are detected instead of the manual palpation, and data can be recorded. These products have been clinically proven to have certain clinical value.

The optical imaging is based on the fact that tissue has different absorption and scattering effects on light of different wavelengths, and thus detecting optical characteristics of the tissue can reflect functional information such as haemoglobin and blood oxygen of the detected tissue, which is of great value for the diagnosis of tumors. However, due to the scattering effect of the detected tissue on the light, the optical imaging has a low spatial resolution, resulting in the poor clinical effect of infrared breast imagers or thermal imagers used in the past. At the same time, the current infrared breast imagers are similar to simple Charged Coupled Device (CCD) cameras, and do not have the function of tomography or volume imaging. It is difficult to obtain information inside the tissue from the CCD images, and it is difficult for the doctor to make a diagnosis from the infrared images. In addition, this type of infrared breast imager also lacks repeatability, and cannot be fused or matched with other images.

SUMMARY

The present invention provides a device for detecting tumors in biological tissue by using a tactile sensor fused with optical tomography. At the same time, physical changes (local hardness) of the tissue and functional changes (blood supply distribution) of the tissue are detected, and tactile images and optical images are fused to improve the detection and diagnosis judgment of breast tumors.

A detection device for tactile sensing and optical tomography, comprising a handheld probe in contact with detected tissue, a controller for performing signal control and data acquisition on the handheld probe and communicating with a computer, and the computer for performing data analysis and image reconstruction and display on controller information, wherein the handheld probe comprises a probe front cover, and a tactile sensor, a probe base, and a photoelectric sensor module disposed in sequence are sandwiched between a first probe side cover and a second probe side cover matching the probe front cover; and an optical fiber connected to the photoelectric sensor module is interposed between the first probe side cover and the second probe side cover.

In particular, a tactile detection thin film is disposed on an end surface of a side of the tactile sensor of the present invention close to the probe front cover, and several optical fiber outlets and low-light detector ports are disposed on the tactile sensor, thereby integrating the detection of two kinds of information on a probe surface.

The photoelectric sensor module of the present invention comprises a photodetector front plate, several low-light detectors and several optical fiber connectors are staggered on a side of the photodetector front plate close to the probe base, a side of the photodetector front plate away from the probe base is provided with a signal processing board, and the low-light detectors are connected to the signal processing board; and an upper terminal of a tactile thin-film sensor and a lower terminal of the tactile thin-film sensor connected to the signal processing board are separately disposed on the tactile sensor.

The controller of the present invention includes a set of light signal generators inside, laser light emitted by the light signal generator is coupled to the optical fiber through an optical switch, and the optical switch controls the light output from different light sources to the optical fiber according to the computer.

A detection method based on the detection device for tactile sensing and optical tomography of the present invention, wherein the tactile sensor acquires signals and sends them to the controller through the photoelectric sensor module, the computer is communicated with the controller, and sends commands to the controller and receives data; and the computer processes received thin-film pressure sensor signals and optical signals to obtain an image of pressure distribution and a light scattering image.

The present invention adopts the above technical solutions and has the following advantages over the prior art.
1. In the present invention, a pressure distribution image and optical Diffuse Optical tomography (DOT) image signals are acquired synchronously, and two three-dimensional images are reconstructed so as to be spatially correlated, which is helpful for the doctor to diagnose diseases in the tissue from both the tactile image and the optical functional image of the tissue, improving the accuracy of diagnosis of tissue diseases.
2. The imaging obtained by the present invention is non-destructive, non-invasive and non-radiative, easy to use, and suitable for the examinations of people of different ages. It is easy to use, and applicable for clinical screening, and has high cost performance and applicability. It can effectively meet the needs of current rapid tumor screening, such as breast cancer screening.
3. In the present invention, a pressure thin-film sensor is used to detect the distribution and change of tissue hardness, which can reflect whether there is a lump or not in a local area (uneven tissue hardness). The optical imaging can reflect the composition information inside the tissue, especially the distribution of blood (oxygenated and deoxygenated blood). Thus, the information on the locations and functions of tissue tumors is provided to assist in the pathological diagnosis of the tumors, for example, the detection and diagnosis of breast cancers.
4. In the present invention, a light signal generator is disposed inside the controller, which can emit laser light of different wavelengths. The laser light emitted by the light signal generator is coupled to the optical fiber through an optical switch. By controlling the optical switch, the controller can select and send required laser signals to one or several optical fibers according to the command requirements of the computer, thereby selecting the sending positions and sending time of the light signals on the handheld sensor. At the same time, the controller communicates with the signal processing board of the handheld probe to coordinate the signal acquisition and processing of the low-light detector, which improves the detection efficiency and improves the accuracy of diagnosis of tissue diseases.
5. In the present invention, a computer is used to be connected to the controller by means of communication (such as a USB port), send commands to the controller and receive data. The received thin-film pressure sensor signals and light signals are processed to obtain an image of pressure distribution and a light scattering image. The pressure distribution image can reflect the consistency and uniformity inside the tissue. If it is used for the examination of breast tissue, an uneven pressure distribution reflects that there is a lump inside the tissue. The light scattering image reflects the absorption of light signals of different wavelengths within the tissue. Based on the principle of tissue optics, laser light of different wavelengths is used. The light scattering image reflects the degree and distribution of absorption of light of different wavelengths by the tissue, so that it is possible to analyze the composition inside the tissue, especially the situation of oxygenated and deoxygenated hemoglobin, which also reflects the metabolic state of the local tissue.
6. In the present invention, the pressure distribution image and the optical image are combined, so that the tissue distribution uniformity (lumps) and the information of local metabolism can be obtained at the same time, which is helpful for the detection and analysis and judgment of benign and malignant of tumors inside the tissue.
7. In the present invention, there are no special requirements and restrictions on the specifications and models of the tactile detection thin film. Different thin-film probes and modules can be selected to assemble with flexibility. The optical detection and control system can use light sources of different wavelengths to detect the reflection of different tissue components. Multiple light sources, a multi-optical-fiber array and a low-light detector array are used to acquire scanning data, and a tissue optical scattering model is used. The infrared imaging unit performs a three-dimensional model reconstruction on a multi-point source tissue scattering image group sequence to obtain a three-dimensional image of the detected tissue. Because tactile imaging and optical imaging are acquired synchronously in the same space, the obtained tactile imaging and optical imaging of the tissue are correlated to each other, and the superposition analysis of images in the two modes is realized for the inspection and diagnosis of the tissue, which is non-destructive, non-invasive and non-radiative.

DETAILED DESCRIPTION OF THE EMBODIMENTS

Figure 1:
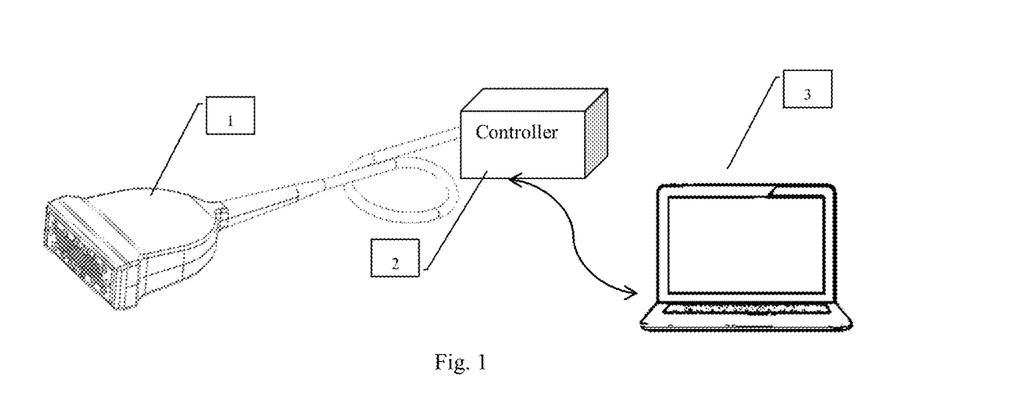
FIG. 1 is a schematic structural diagram of the present invention.
Figure 2:
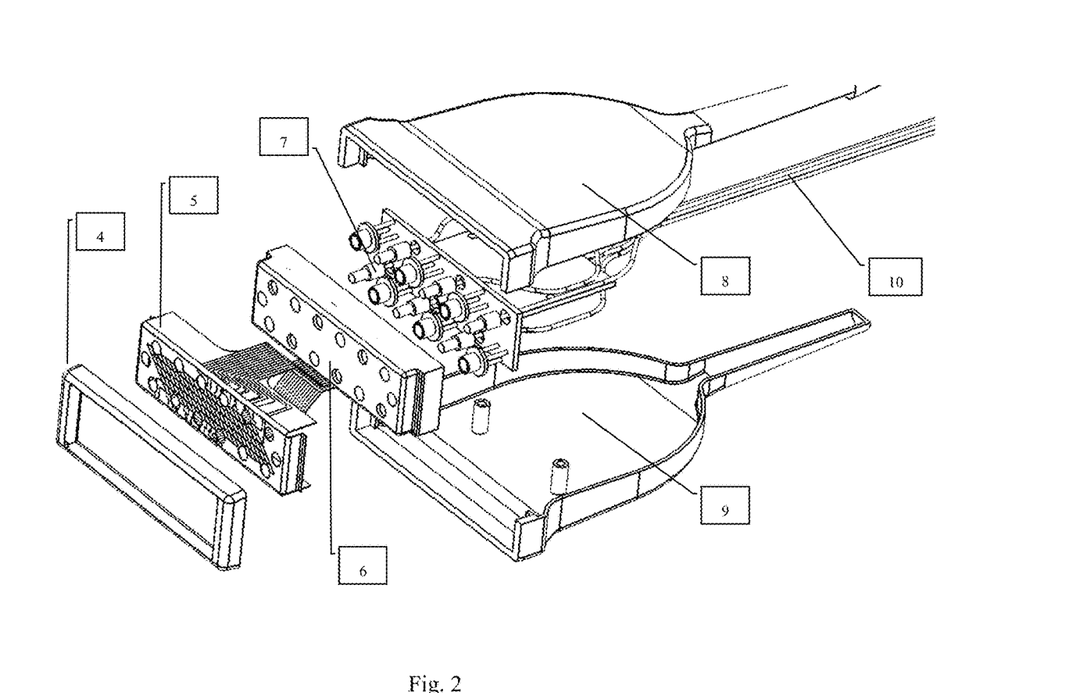
FIG. 2 is a schematic structural diagram of a handheld probe of the present invention.

The technical solutions of the present invention are further described in detail below in conjunction with the drawings:

As shown in FIGS. 1 and 2, a detection device for tactile sensing and optical tomography includes the handheld probe 1 in contact with detected tissue, the controller 2 for performing signal control and data acquisition on the handheld probe and communicating with a computer, and the computer 3 for performing data analysis and image reconstruction and display on controller information. The handheld probe 1 includes the probe front cover 4. The tactile sensor 5, the probe base 6, and the photoelectric sensor module 7 disposed in sequence are sandwiched between the first probe side cover 8 and the second probe side cover 9 matching the probe front cover 4. The optical fiber 10 connected to the photoelectric sensor module 7 is interposed between the first probe side cover 8 and the second probe side cover 9.

Figure 3:
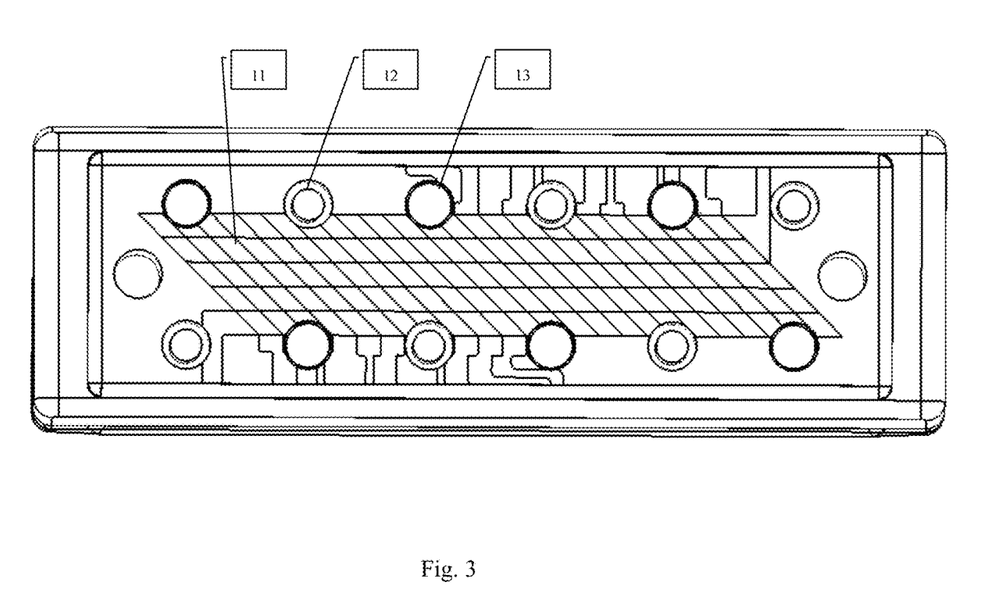
FIG. 3 is a schematic structural diagram of an end surface structure of a tactile sensor of the present invention.

As shown in FIG. 3, the tactile detection thin film 11 is disposed on an end surface of a side of the tactile sensor 5 of the present invention close to the probe front cover 4, and several optical fiber outlets 12 and low-light detector ports 13 are disposed on the tactile sensor 5.

Figure 4:
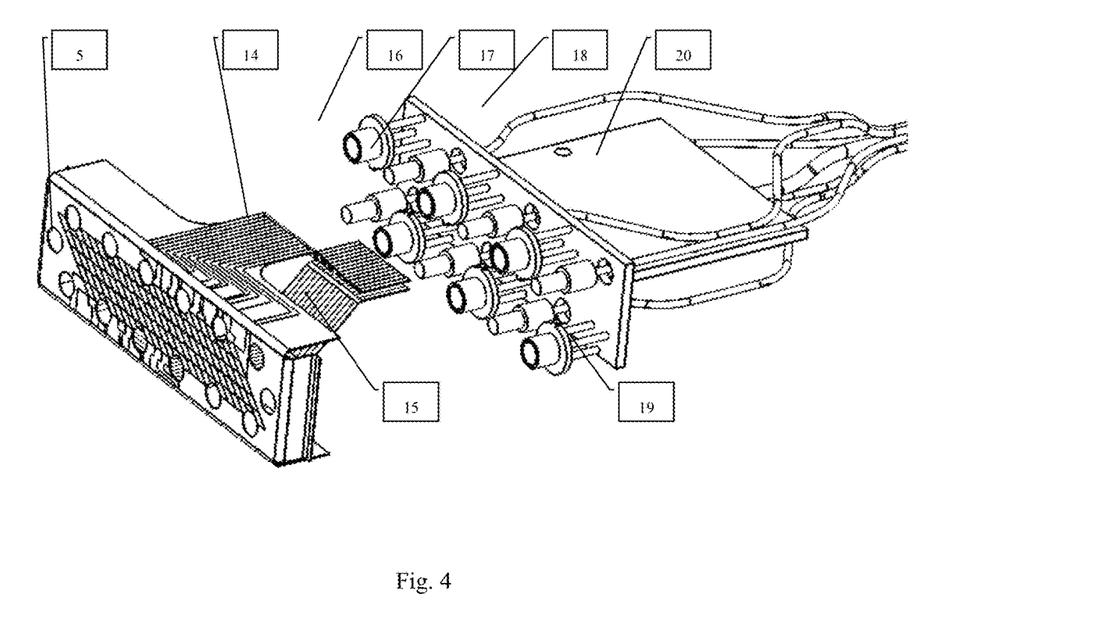
FIG. 4 is a schematic structural diagram of the tactile sensor of the present invention.

As shown in FIG. 4, the photoelectric sensor module 7 of the present invention includes the photodetector front plate 19. Several low-light detectors 16 and several optical fiber connectors 17 are staggered on a side of the photodetector front plate 19 close to the probe base 6. A side of the photodetector front plate 19 away from the probe base 6 is provided with the signal processing board 20, and the low-light detectors 16 are connected to the signal processing board 20. The upper terminal 14 of a tactile thin-film sensor and the lower terminal 15 of the tactile thin-film sensor connected to the signal processing board 20 are separately disposed on the tactile sensor 5.

The controller of the present invention includes a set of light signal generators inside, and laser light emitted by the light signal generator is coupled to the optical fiber through an optical switch.

Figure 5:
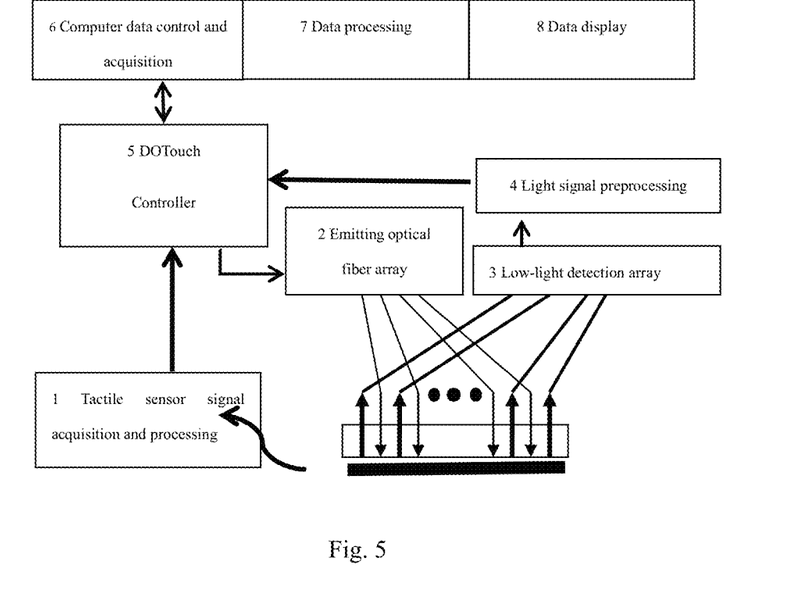
FIG. 5 is a block diagram of the working principle of the present invention.

As shown in FIG. 5, the tactile sensor 5 of the present invention acquires signals and sends them to the controller 2 through the photoelectric sensor module 7. The computer 3 is communicated with the controller 2, and sends commands to the controller 2 and receives data. The computer 3 processes received thin-film pressure sensor signals and optical signals to obtain an image of pressure distribution and a light scattering image.

As shown in FIG. 5, the controller 2 of the present invention sends signals to the photoelectric sensor module 7. The photoelectric sensor module 7 sends laser light to the tissue to be detected through an optical fiber array. The tactile sensor 5 acquires light signals emitted by the tissue to be detected and sends them to the controller 2. The controller 2 sends the acquired light signals and tactile sensor information to the computer 3.

In a detection method based on the detection device for fusion of tactile sensing and optical tomography of the present invention, the tactile sensor acquires signals and sends them to the controller through the photoelectric sensor module, the computer is communicated with the controller, sends commands to the controller and receives data, and the computer processes received thin-film pressure sensor signals and optical signals to obtain an image of pressure distribution and a light scattering image.

The controller of the present invention sends signals to the photoelectric sensor module, the photoelectric sensor module sends laser light of various wavelengths to tissue to be detected through an optical fiber array in a time-sharing manner, the low-light detector acquires light signals and then sends them to the controller, and the controller sends the acquired light signals and tactile sensor information to the computer.

The signal obtained by the tactile sensor of the present invention is a pressure value of each detection point of spatial distribution of a contact surface, and according to a dot matrix distribution of a thin-film pressure sensor and the value of each point, the computer obtains a hardness distribution of the tissue in contact with a detection surface, which is presented as a three-dimensional hardness distribution image, and reflects lumps inside soft tissue.

In the present invention, light of various wavelengths enters the tissue from multiple locations, after it is absorbed and scattered inside the tissue, output light information is obtained at multiple locations, and the computer obtains the information of the low-light detector, and then uses a light scattering tomography imaging method to obtain a light scattering tomography image, thereby obtaining a light absorption distribution image inside the detected tissue; and the absorption of various light signals on the detected tissue reflects blood supply inside the detected tissue.

The computer of the present invention displays the obtained three-dimensional hardness distribution image and light scattering tomography image in real time, and during use, a user dynamically observes tactile changes of the tissue and optical characteristics of the tissue, thereby discovering tumors inside the tissue and their features.

Figure 6:
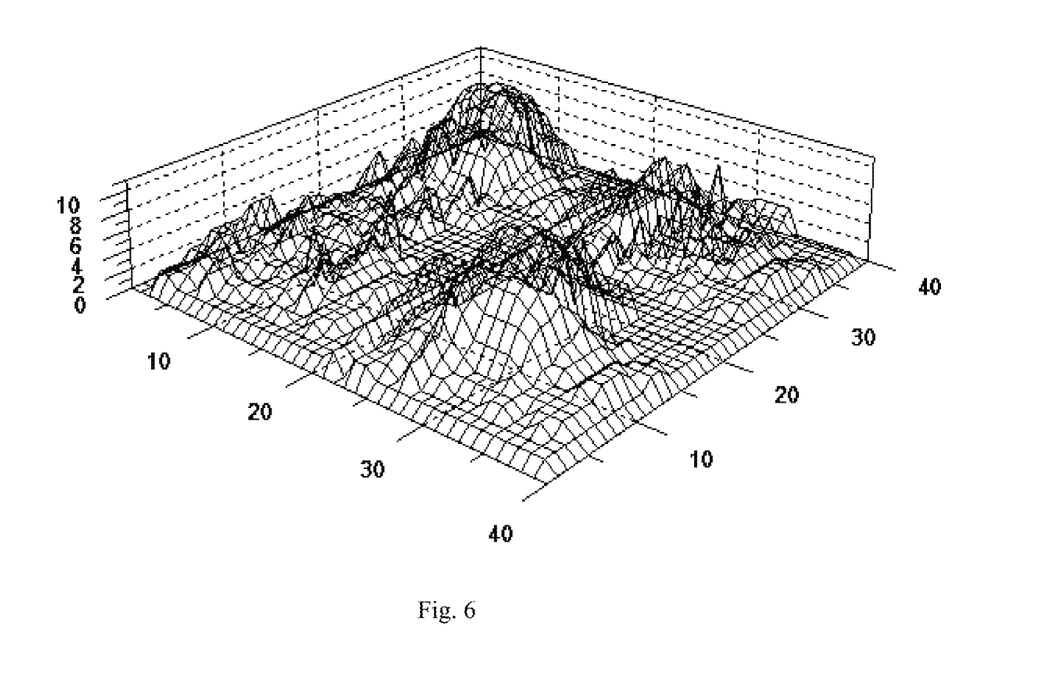
FIG. 6 is an image display of the present invention after pressure detection is performed using a thin-film pressure sensor.

The thin-film pressure sensor of the present invention includes a plurality of separate pressure measurement points, forming a planar distribution array on a contact surface. Each measurement point detects a pressure value of the contact point. By putting all the pressure values together, the sensor array reflects a pressure distribution on this contact surface. For the detected pressure distribution data, after processing, it may be expressed by spatial three-dimensional data (as shown in FIG. 6), or may be expressed in a form of a plane pseudo-color image. Both can reflect the pressure distribution on the detected tissue surface. For the detection of breast tissue, it can reflect whether there is a lump or not inside the breast, as well as its location and size.

Figure 7:
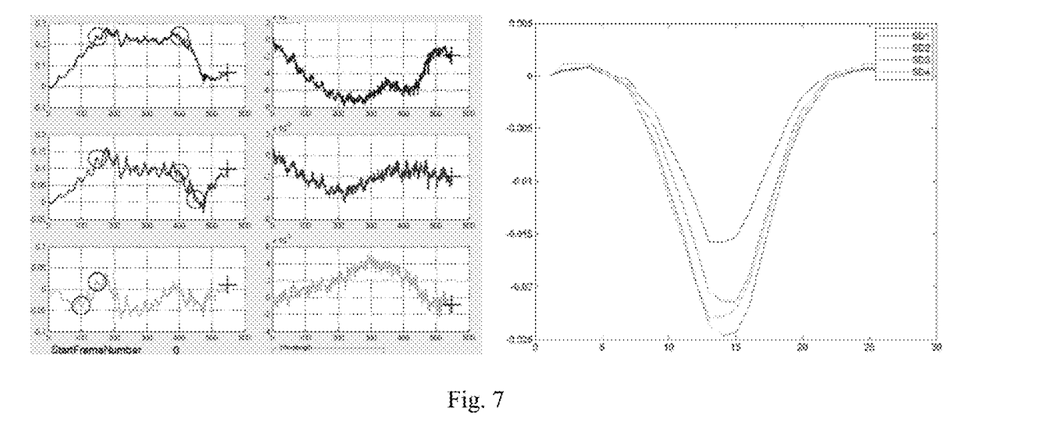
FIG. 7 is a data display of the present invention after detection is performed using a micro-photoelectric sensor module.

A light detection module includes a plurality of spatially distributed output optical fibers and spatially distributed low-light detectors. In a typical application, the controller selects a laser light source of a wavelength and an output optical fiber, and then detects signals of all the low-light detectors. The signal of each low-light detector reflects that after a light wavelength and a light-emitting point are given, emitted photons pass through the detected tissue, and are scattered to obtain an output light signal at each low-light detector position (as shown in FIG. 7). If the controller contains J laser sources, and the probe has N output optical fibers and M low-light detectors, then J×N×M sets of signals may be acquired. These signals can be displayed in real time. When the handheld probe is moved, an operator can observe signal changes at each position.

Figure 8:
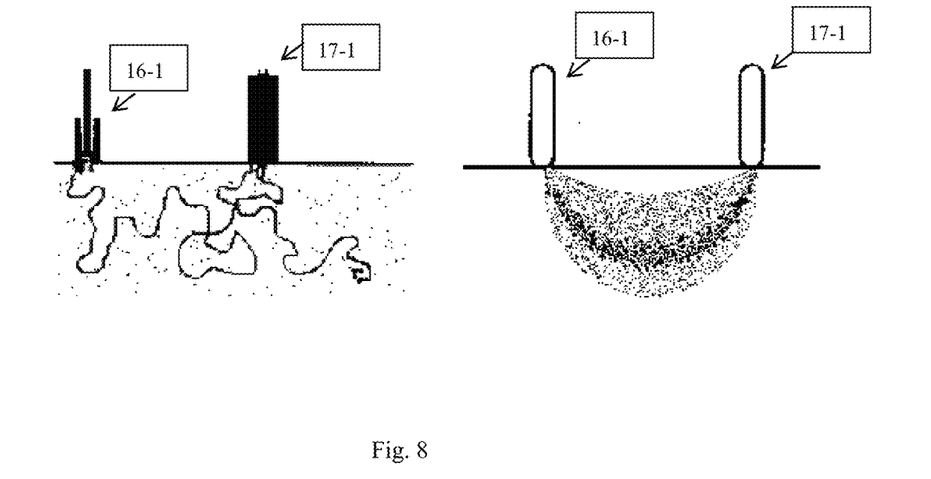
FIG. 8 is a schematic diagram of a path of light scattering after a light signal enters tissue.
Figure 9:
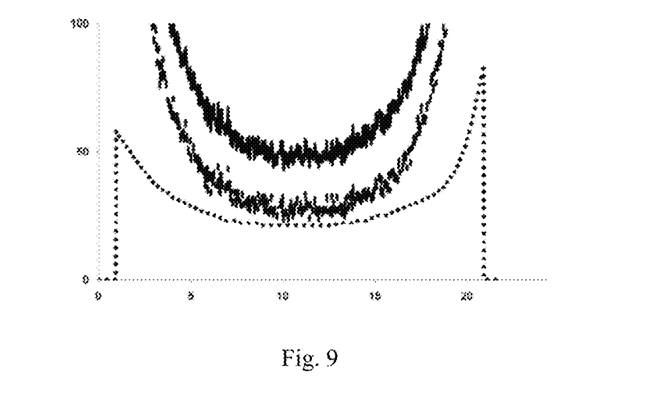
FIG. 9 is an image display of the present invention obtained after reconstruction is performed according to a DOT algorithm.

When a beam of light enters an uniform tissue, the tissue interacts with the incoming photons, of which a part is absorbed, a part is scattered and then enters the tissue, and the other part returns to the tissue surface. The overall light scattering path is similar to a banana shape (as shown in FIG. 8). At different distances from the emitting light source point to the receiving detector point, the resulting signals reflect light scattering and absorption at different tissue depths (as shown in FIG. 9). In bio-optics, its laws are described by a set of transport equations (mechanisms) for photon scattering.

Figure 10:
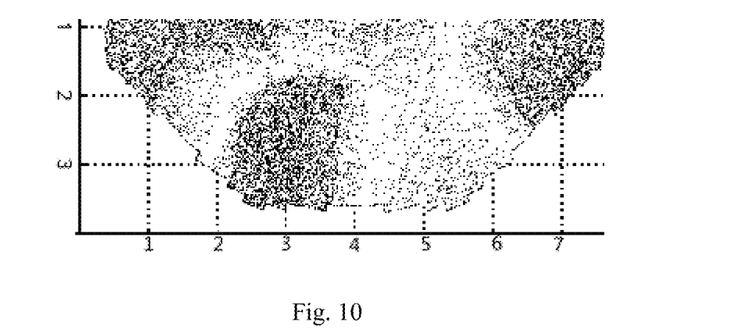
FIG. 10 is a schematic diagram where a thin-film tactile sensor of the invention uses 16-channel data parallel acquisition.

Based on a scattering model of tissue optics, the acquired J×N×M sets of signals can be used to perform image reconstruction, obtaining an image of scattering and absorption distribution of characteristic light bands by the tissue. The image provides the metabolic situation of the local tissue (as shown in FIG. 10).

Figure 11:
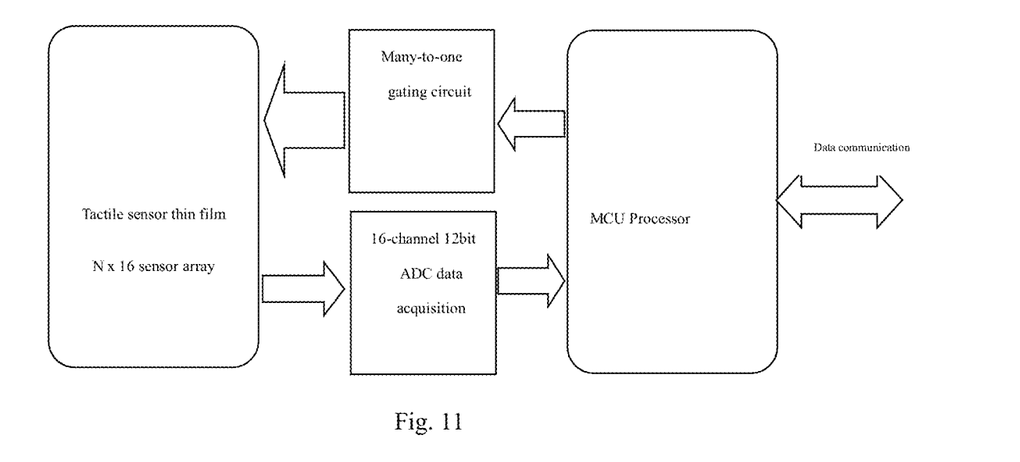
FIG. 11 is a schematic diagram of a working state of a photoelectric sensor module of the present invention.

The thin-film tactile sensor of the present invention adopts single-line scanning and acquires data in parallel by multi-channel signals, which can quickly obtain pressure signal values on all distribution points in real time, thereby obtaining a pressure distribution on the overall contact surface. The circuit design is completed by a micro-processing chip. FIG. 11 shows a schematic diagram of multi-channel signal gating and parallel acquisition of 16-channel data.

Figure 12:
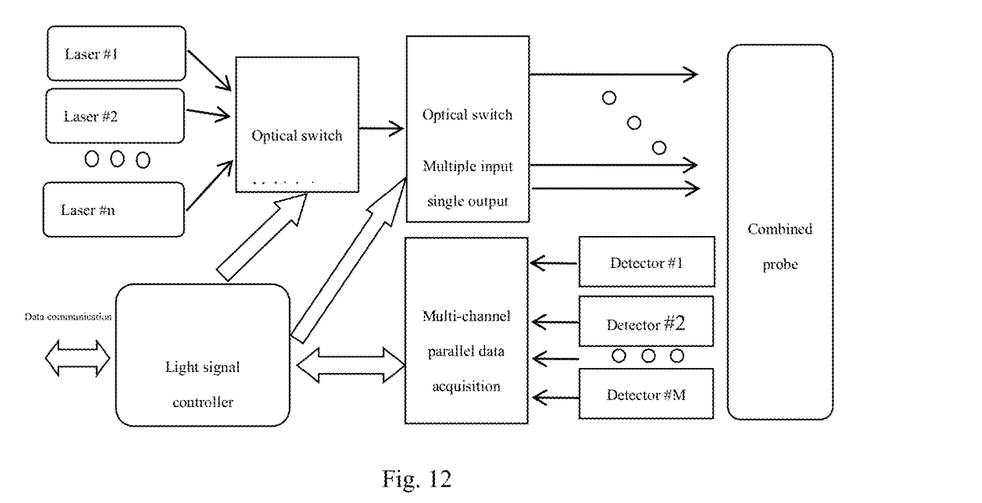
FIG. 12 is a schematic diagram of a DOT imaging state of the present invention.

FIG. 12 represents a structure for control of light signals and data acquisition of the present invention. In order to obtain DOT imaging of tissue and information on light of different wavelengths of the tissue, the data acquisition method of the optical system is as follows:
1) the light signal controller controls a light source selection optical switch to select a light source of a predetermined wavelength, and transmits signals to an output selection optical switch;
2) the light signal controller controls a control output selection optical switch to select an optical fiber output light signal to the probe, controls to acquire signals from all low-light detectors in parallel, and saves them;
3) the light signal controller controls the control output selection optical switch to select the next optical fiber output light signal to the probe, controls to acquire signals from all low-light detectors in parallel, and saves them;
4) when all optical fiber outputs are traversed and all the signals are acquired, the light signal controller controls the light source selection optical switch to select the next light source signal, and the above processes of 2-3 are repeated until all light source signals are completed; and
5) after a set of data is acquired, a host computer performs data analysis and calculation to obtain optical tomography (DOT) of the tissue at the current position.

The basic principle of the DOT imaging of the present invention is as follows: given a time-space distribution of a light source on a surface of a tissue body and a time-space distribution of a corresponding measured amount of transmitted light, a three-dimensional distribution of optical parameters in the tissue body is solved based on a predetermined photon transmission model. The task of DOT imaging is to simultaneously reconstruct the distribution of all optical parameters in the tissue domain. In applications, it is often assumed that one or two parameter distributions (usually the refractive index) are known constants to simplify the solution of the problem, that is, only absorption and reduced scattering coefficients are usually reconstructed.

The DOT imaging calculation of the present invention depends on the following several factors: signal intensity of the light-emitting source, sensitivity of the low-light detector, and a relative position of the light-emitting source and the detector. The relative position is determined by the geometry of a desk. The information in the first two aspects is calibrated using a standard substance before the system is used.

An imaging algorithm of DOT is the Boltzmann transport equation based on the scattering model, i.e. the photon scattering model:

$$\frac{\partial \Phi(r, t)}{\partial t} = D\nabla^2 \Phi(r, t) - v\mu_a \Phi(r, t) + vS(r, t)$$

where $\Phi(r,t)$ is a photon flux (photons/[cm$^2$·s]); v is a speed of light in a scattering solution; $\mu_a$ is an absorption coefficient; $\mu_s'=(1-g)\mu_s$ is a reduced scattering coefficient, r is "an average cosine of scattering angles"; $D=v/3\mu_s'$ is a photon scattering degree; and $S(r,t)$ is an in-phase light source. The model assumes that the input light source is a high-frequency signal (high-frequency modulated light signal), and uses it to have frequency and phase information.

The acquired data can be used to inversely solve the transport equation according to the intensity of the light signal itself, the detected signal, and the spatial distribution information, thereby obtaining the light absorption and scattering DOT distribution of a predetermined light wavelength by the detected tissue. If the blood distribution in the tissue is uniform, then the distribution image of DOT will be uniformly distributed. If there is local accumulation of blood in the tissue, then the absorption of light signals by this part will change (the absorption increases), DOT imaging will reflect the high absorption value in this area, and the image display changes.

What is claimed is:

1. A detection device for fusion of tactile sensing and optical tomography, comprising a handheld probe, a controller and a computer, wherein,
the handheld probe is configured to be in contact with detected tissue, the controller is configured to perform signal control and data acquisition on the handheld probe and communicate with the computer, and the computer is configured to perform data analysis, image reconstruction and display information from the controller;
the handheld probe comprises a probe front cover, a tactile sensor, a probe base, and a photoelectric sensor module, wherein the tactile sensor, the probe base, and the photoelectric sensor module are disposed in sequence and are sandwiched between a first probe side cover and a second probe side cover, and the first probe side cover and the second probe side cover match the probe front cover; and
an optical fiber connected to the photoelectric sensor module is interposed between the first probe side cover and the second probe side cover,
wherein the controller is further configured to:
send a first instruction signal to the photoelectric sensor module causing the photoelectric sensor module to send a first transmission of laser light of a first wavelength to the detected tissue through an optical fiber array via a first fiber optic output of a plurality of fiber optic outputs,
receive first light signals corresponding to the first transmission from a plurality of low-light detectors, the plurality of low-light detectors acquiring the first light signals as tissue light scattering results of the first transmission of laser light,
send a second instruction signal to the photoelectric sensor module causing the photoelectric sensor module to select a second optical fiber output of the plurality of fiber optic outputs and to send a second transmission of laser light of the first wavelength to the detected tissue via the second optical fiber output, receive second light signals corresponding to the second transmission from the plurality of low-light detectors, the plurality of low-light detectors acquiring the second light signals as tissue light scattering results of the second transmission of laser light, and after transmitting laser light of the first wavelength over the plurality of fiber optic outputs, send a series of third instruction signals to the photoelectric sensor module causing the photoelectric sensor module to sequentially select optical fiber outputs of the plurality of fiber optic outputs and to sequentially send transmissions of laser light of a second wavelength to the detected tissue via the sequentially selected optical fiber outputs, corresponding third light signals being acquired by the plurality of low-light detectors and sent to the controller;

wherein a tactile detection thin film is disposed on a side of the tactile sensor facing the probe front cover, and a plurality of optical fiber outlets and a plurality of low-light detector ports are disposed interleaved among sensing points of the tactile sensor, wherein the tactile sensor comprises the tactile detection thin film with distributed sensing point arrays.

2. The detection device according to claim 1, wherein the photoelectric sensor module comprises a photodetector front plate, the plurality of low-light detectors and a plurality of optical fiber connectors are staggered on a side of the photodetector front plate facing the probe base, a side of the photodetector front plate on facing away from the probe base is provided with a signal processing board, and the plurality of low-light detectors are connected to the signal processing board, and an upper terminal of the tactile sensor and a lower terminal of the tactile sensor are connected to the signal processing board.

3. The detection device according to claim 1, wherein the controller comprises a set of light signal generators, the set of light signal generators is provided inside the controller, and laser light emitted by the set of light signal generator is coupled to the optical fiber through an optical switch.

4. A detection method based on the detection device according to claim 1, comprising:

enabling the tactile sensor to acquire thin-film pressure sensor signals and send the thin-film pressure sensor signals to the controller;

communicating between the computer and the controller, and enabling the computer to send commands to the controller and receive data; and enabling the computer to process the received thin-film pressure sensor signals to obtain an image of pressure distribution and process the first light signals, the second light signals and the third light signals to obtain a light scattering tomography image.

5. The detection method according to claim 4, wherein the controller sends the first light signals, the second light signals, the third light signals, and the thin-film pressure sensor signals to the computer.

6. The detection method according to claim 4, wherein the thin-film pressure sensor signals obtained by the tactile sensor is a pressure value of each detection point of spatial distribution of a contact surface, and according to a dot matrix distribution of the tactile sensor and the pressure value of the each detection point, the computer obtains a hardness distribution of the detected tissue in contact with a detection surface, the hardness distribution of the detected tissue is presented as a three-dimensional hardness distribution image, and reflects lumps inside soft tissue.

7. The detection method according to claim 5, wherein the laser light of various wavelengths, the various wavelengths including the first wavelength and the second wavelength, enters the detected tissue from a plurality of locations, after the laser light of various wavelengths is absorbed and scattered inside the detected tissue, output light information including the first light signals, the second light signals and the third light signals is obtained at the plurality of locations, and the computer obtains the output light information, and then uses a light scattering tomography imaging method to obtain h light scattering tomography image, and to obtain a light absorption distribution image inside the detected tissue; and absorption of various light signals on the detected tissue reflects blood supply/distribution inside the detected tissue.

8. The detection method according to claim 6, wherein the computer displays the three-dimensional hardness distribution image and the light scattering tomography image in real time, and during use, a user dynamically observes tactile changes of the detected tissue and optical characteristics of the detected tissue, to discover tumors inside the detected tissue and features of the tumors.

9. The detection method according to claim 7, wherein the computer displays a three-dimensional hardness distribution image and the light scattering tomography image in real time, and during use, a user dynamically observes tactile changes of the detected tissue and optical characteristics of the detected tissue, to discover tumors inside the detected tissue and features of the tumors.

10. The detection device according to claim 1, wherein the plurality of fiber optic outputs is greater than two.

11. The detection device according to claim 1, wherein a number of different wavelengths transmitted is greater than two.

12. The detection device according to claim 1,
wherein the controller comprises J laser sources, J being a whole number greater than 1,
wherein the handheld probe comprises N output optical fibers and M low-light detectors, N and M being whole numbers greater than 1,
wherein the controller is further configured to receive J×N×M sets of signals.

13. A detection device for fusion of tactile sensing and optical tomography, comprising a handheld probe, a controller and a computer, wherein, the handheld probe is configured to be in contact with detected tissue, the controller is configured to perform signal control and data acquisition on the handheld probe and communicate with the computer, and the computer is configured to perform data analysis, image reconstruction and display information from the controller;

the handheld probe comprises a probe front cover, a tactile sensor, a probe base, and a photoelectric sensor module, wherein the tactile sensor, the probe base, and the photoelectric sensor module are disposed in sequence and are sandwiched between a first probe side cover and a second probe side cover, and the first probe side cover and the second probe side cover match the probe front cover; and an optical fiber connected to the photoelectric sensor module is interposed between the first probe side cover and the second probe side cover, wherein the controller is further configured to:
send a first instruction signal to the photoelectric sensor module causing the photoelectric sensor module to send a first transmission of laser light of a first wavelength to the detected tissue through an optical fiber array via a first fiber optic output of a plurality of fiber optic outputs, receive first light signals corresponding to the first transmission from a plurality of low-light detectors, the plurality of low-light detectors acquiring the first light signals as tissue light scattering results of the first transmission of laser light, send a second instruction signal to the photoelectric sensor module causing the photoelectric sensor module to select a second optical fiber output of the plurality of fiber optic outputs and to send a second transmission of laser light of the first wavelength to the detected tissue via the second optical fiber output, receive second light signals corresponding to the second transmission from the plurality of low-light detectors, the plurality of low-light detectors acquiring the second light signals as tissue light scattering results of the second transmission of laser light, and after transmitting laser light of the first wavelength over the plurality of fiber optic outputs, send a series of third instruction signals to the photoelectric sensor module causing the photoelectric sensor module to sequentially select optical fiber outputs of the plurality of fiber optic outputs and to sequentially send transmissions of laser light of a second wavelength to the detected tissue via the sequentially selected optical fiber outputs, corresponding third light signals being acquired by the plurality of low-light detectors and sent to the controller:

wherein the tactile sensor comprises a tactile detection thin film and the tactile detection thin film is disposed on a side of the tactile sensor facing the probe front cover, and a plurality of optical fiber outlets and a plurality of low-light detector ports are disposed in openings of the tactile detection thin film on the side of the tactile sensor facing the probe front cover.

14. A detection method for fusion of tactile sensing and optical tomography, comprising:

acquiring thin-film pressure sensor signals by a tactile sensor, a tactile detection thin film being disposed on a side of the tactile sensor facing the probe front cover, a plurality of optical fiber outlets and a plurality of low-light detector ports being disposed interleaved among sensing points of the tactile sensor, and the tactile sensor comprising the tactile detection thin film with distributed sensing point arrays;

receiving the thin-film pressure sensor signals at a controller which also controls a photoelectric sensor module;

performing signal control and data acquisition on a handheld probe using the controller and communicating with a computer, the computer being configured to perform data analysis, image reconstruction and display information from the controller;

sending a first instruction signal to the photoelectric sensor module causing the photoelectric sensor module to send a first transmission of laser light of a first wavelength to detected tissue through an optical fiber array via a first fiber optic output of a plurality of fiber optic outputs;

receiving first light signals corresponding to the first transmission from a plurality of low-light detectors, the plurality of low-light detectors acquiring the first light signals;

sending a second instruction signal to the photoelectric sensor module causing the photoelectric sensor module to select a second optical fiber output of the plurality of fiber optic outputs and to send a second transmission of laser light of the first wavelength to the detected tissue via the second optical fiber output;

receiving second light signals corresponding to the second transmission from the plurality of low-light detectors, the plurality of low-light detectors acquiring the second light signals; and after transmitting laser light of the first wavelength over the plurality of fiber optic outputs, sending a series of third instruction signals to the photoelectric sensor module causing the photoelectric sensor module to sequentially select optical fiber outputs of the plurality of fiber optic outputs and to sequentially send transmissions of laser light of a second wavelength to the detected tissue via the sequentially selected optical fiber outputs, corresponding third light signals being acquired by the plurality of low-light detectors and sent to the controller.

\* \* \* \* \*